(12) United States Patent
Burton, Sr. et al.

(10) Patent No.: US 7,943,670 B2
(45) Date of Patent: May 17, 2011

(54) LIQUID FORMULATIONS OF RACTOPAMINE

(75) Inventors: Michael David Burton, Sr., Greenfield, IN (US); Paul Reuben Klink, Greenfield, IN (US)

(73) Assignee: Eli Lilly and Company, Indianapolis, IN (US)

( * ) Notice: Subject to any disclaimer, the term of this patent is extended or adjusted under 35 U.S.C. 154(b) by 594 days.

(21) Appl. No.: 10/571,437

(22) PCT Filed: Oct. 4, 2004

(86) PCT No.: PCT/US2004/030902
§ 371 (c)(1),
(2), (4) Date: Mar. 13, 2006

(87) PCT Pub. No.: WO2005/036980
PCT Pub. Date: Apr. 28, 2005

(65) Prior Publication Data
US 2007/0042022 A1  Feb. 22, 2007

(51) Int. Cl.
*A01N 31/14* (2006.01)
*A61K 31/075* (2006.01)
(52) U.S. Cl. ..................................................... 514/721
(58) Field of Classification Search ................... 514/721
See application file for complete search history.

(56) References Cited

U.S. PATENT DOCUMENTS 4,690,951 A    9/1987  Anderson et al.
6,231,887 B1 *  5/2001  Gao et al. ....................... 424/451

FOREIGN PATENT DOCUMENTS

GB    2029407    *  7/1979
WO    WO 02/18436    3/2002

OTHER PUBLICATIONS

Watkins et al, The Effect of Various Levels of Ractopamine Hydrochloride on the Performance and Carcass Characteristics of Finishing Swine, J. Anim Sci. 1990 68: 3588-3595.*
Strickley, Robert G., "Solubilizing excipients in oral and injectable formulations," *Pharmaceutical Research*, 21(2):201-230 (Feb. 2004).
Uttaro, B., et al., "Effect of ractopamine and sex on growth, carcass characteristics, processing yield, and meat quality characteristics of crossbred swine," *Journal of Animal Science*, 71(9):2349 (1993).

* cited by examiner

*Primary Examiner* — Frederick Krass
*Assistant Examiner* — Benjamin Packard
(74) *Attorney, Agent, or Firm* — James J. Sales; John C. Demeter

(57) ABSTRACT

Described is a soluble stable liquid formulation, process for preparing, and a method of using the soluble stable liquid formulation comprising ractopamine or a physiologically acceptable salt thereof, a liquid nonionic cosolvent, and water.

9 Claims, No Drawings

LIQUID FORMULATIONS OF RACTOPAMINE

BACKGROUND OF THE INVENTION

Ractopamine is a swine feed ingredient that directs nutrients to improve production efficiencies and increase carcass lean gain. Ractopamine has been approved by the United States Food and Drug Administration (FDA) and registered for use in swine and in cattle. Efficacy studies have demonstrated the effectiveness of ractopamine in increasing carcass leanness, increasing rate of weight gain, and improving feed efficiency through testing in swine and cattle in the United States and other countries around the world. These data have established that pork and beef from ractopamine-fed animals is safe for human consumption, and the FDA approved the product after thoroughly reviewing all data to ensure that it met their stringent human food safety standards. Currently, ractopamine is approved for use in the United States and several other countries. Ractopamine is becoming an accepted tool by the swine and beef industry to improve the production of high value lean pork and beef, and at the same time, reduce the environmental impact of each kilogram of pork and beef produced.

Ractopamine is the United States Adopted Name for the compound (1-(4-hydroxyphenyl)-2-(1-methyl-3-(4-hydroxyphenyl)propylamino)ethanol having the following structure of formula I:

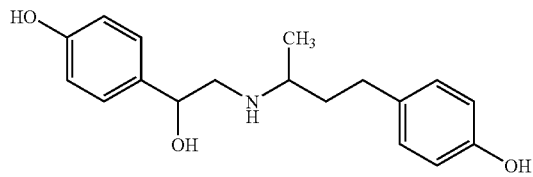

It has two asymmetric carbon atoms. The R,R isomer is the most active, but other isomers are also active. Although an individual isomer can be isolated, an individual isomer is not required and preferably the compound is employed as a mixture of the isomers. Various physiologically acceptable salts of ractopamine are possible and the hydrochloride salt is preferred. Ractopamine is a selective beta-one adrenergic receptor agonist.

U.S. Pat. No. 4,690,951 discloses ractopamine, various formulations of ractopamine, uses of ractopamine, and processes for making ractopamine.

The present commercially available formulation is a solid dry premix (Type A medicated article) comprising 9 g per pound (20 g/kg) of ractopamine hydrochloride with ground corncobs. Said dry premix is then thoroughly mixed by the consumer into appropriate solid feed ingredients to obtain ractopamine hydrochloride amounts of 9-18 grams/ton.

As recently approved for cattle, the commercial formulation for cattle is also a solid dry premix comprising 45.4 g per pound of ractopamine hydrochloride with ground corncobs. This dry premix may be thoroughly mixed by the consumer into appropriate solid feed ingredients to afford 8.2 to 24.6 g/ton of ractopamine hydrochloride for administration to cattle. Also included are directions for mixing the solid dry premix into liquid Type B feeds to afford a liquid Type B medicated feed comprising from 0.82 to 1.15 grams/pound or 0.18 to 0.25% by weight of ractopamine hydrochloride. The pH in the liquid Type B feed is required to be maintained at between 4.5 and 7.5. Daily recirculation is required, as well as recirculation immediately prior to use.

Ractopamine, and its hydrochloride salt, have limited solubility in water of about 3-4% by weight. Adjusting pH with acid or base or suitable buffer does not substantially increase solubility of ractopamine. Although the solid premix, as noted above, is becoming an accepted tool by the swine industry to improve production of high value lean pork, there remains a substantial need for a solution type formulation to expand the potential ways by which ractopamine hydrochloride may be administered. Sick livestock, for example, cannot always be induced to eat solid dry feed.

Enhanced solubility of ractopamine hydrochloride can be obtained in certain alcohol and glycol solvents. This enhanced solubility of greater than 3-4%, however, is achieved at the expense of stability problems. As noted above, ractopamine has three hydroxyl groups bonded to the molecule. The molecule is reactive at the hydroxyl group bonded to the divalent ethan-1,2-diyl moiety. When ractopamine is dissolved in an alcohol, glycol or other polar solvents, the molecule reacts at the ethan-1,2-diyl hydroxy group with the hydroxy group of the solvent to form covalently bonded reaction products. The formation and presence of such reaction products is highly undesirable because the pharmacological properties including safety, and toxicologic properties of such reaction products have not been characterized. Further, such reaction products may adversely impact one or more of the requirements under the United States Food and Drug Administration, FDA Center for Veterinary Medicine, Guideline Nos. 92 and 93 Impurities in New Veterinary Drug Substances and Impurities in New Veterinary Medicinal Products, incorporated herein by reference.

Investigations into the solubility of ractopamine hydrochloride in nonpolar solvents evidenced insufficient solubility for purposes of creating a useful Type A liquid formulation. Surprisingly, it has been found that certain cosolvents can be employed to afford solubility of ractopamine hydrochloride and acceptable stability suitable for a liquid formulation.

Accordingly, one object of the present invention is to provide improved solubilization and stabilization of ractopamine or a physiologically acceptable salt thereof. A further object of the present invention is to provide stable liquid solutions and formulations comprising ractopamine or a physiologically acceptable salt thereof in association with certain cosolvents. A further object of the invention is to provide a process for the preparation of a stabilized liquid formulation.

Other objects, features and advantages will become apparent to those skilled in the art from the following description and claims.

BRIEF SUMMARY OF THE INVENTION

The present invention relates to a solubilized stabilized liquid formulation comprising from 5 to 30% w/w of ractopamine or a physiologically acceptable salt thereof; from 20 to 90% w/w of a liquid nonionic cosolvent selected from polyethoxylated sorbitan fatty acid esters, polyethoxylated vegetable oils, or both; and, from 5 to 75% w/w water.

The present invention also relates to processes of making a solubilized stabilized liquid formulation comprising from 5 to 30% w/w of ractopamine or a physiologically acceptable salt thereof; from 20 to 90% w/w of a liquid nonionic cosolvent selected from polyethoxylated sorbitan fatty acid esters, polyethoxylated vegetable oils, or both; and, from 5 to 75% w/w water by first admixing the ingredients and heating to no higher than 100° C.

The present invention also relates to methods of using a solubilized stabilized liquid formulation comprising from 5 to 30% w/w of ractopamine or a physiologically acceptable salt thereof; from 20 to 90% w/w of a liquid nonionic cosolvent selected from polyethoxylated sorbitan fatty acid esters, polyethoxylated vegetable oils, or both; and, from 5 to 75% w/w water for increasing weight gain, improving the efficiency of feed utilization, increasing leanness, decreasing lipogenesis, increasing lipolysis, increasing muscle protein synthesis, decreasing muscle protein breakdown or improving carcass quality of a ruminant, a swine, or a turkey comprising orally administering to the ruminant, swine or turkey an effective amount of a solubilized stabilized liquid formulation of the present invention.

DETAILED DESCRIPTION OF THE INVENTION

The present invention resides in the unexpected stabilized and solubilized aqueous solution of ractopamine or a physiologically acceptable salt thereof prepared with water and a liquid nonionic cosolvent selected from polyethoxylated sorbitan fatty acid esters, polyethoxylated vegetable oils, or both. Considering the low solubility, instability, or both, described above when ractopamine was dissolved in polar solvents, it is surprising that a stabilized, solubilized aqueous solution of ractopamine or a physiologically acceptable salt thereof is afforded when combined with water and the stated liquid nonionic cosolvents.

The present invention relates to a solubilized, stabilized liquid formulation comprising from 5 to 30% w/w of ractopamine or a physiologically acceptable salt thereof; preferably 10 to 20% and more preferably 10 to 15%; from 20 to 90% w/w of a liquid nonionic cosolvent selected from polyethoxylated sorbitan fatty acid esters, polyethoxylated vegetable oils, or both, preferably 30 to 80% and more preferably 40 to 55%; and, from 5 to 75% w/w water, preferably 10 to 60% and more preferably 35 to 50%. A preferred solubilized, stabilized liquid formulation of the present invention is 10 to 20% ractopamine or a physiologically acceptable salt thereof, 30 to 80% of said cosolvent, and 10 to 60% water. A more preferred solubilized, stabilized liquid formulation of the present invention is 10 to 15% ractopamine or a physiologically acceptable salt thereof, 40 to 55% of said cosolvent, and 35 to 50% water. Among the polyethoxylated sorbitan fatty acid esters, polyethoxylated 20 sorbitan monolaurate or monooleate are preferred. Among the polyethoxylated vegetable oils, polyethoxylated castor oil is preferred and polyethoxylated 35 castor oil is most preferred.

A further object of the invention is to provide a process for the preparation of a solubilized, stabilized liquid formulation comprising: admixing ractopamine or a physiologically acceptable salt thereof with water and a liquid nonionic cosolvent selected from polyethoxylated sorbitan fatty acid esters, polyethoxylated vegetable oils, or both; and heating the mixture to no higher than 100° C., preferably no higher than 60° C., to afford a stabilized and solubilized formulation comprising from 5 to 30% w/w ractopamine or a physiologically acceptable salt thereof; from 20 to 90% w/w of a liquid nonionic cosolvent selected from polyethoxylated sorbitan fatty acid esters, polyethoxylated vegetable oils, or both; and, from 5 to 75% w/w water.

A further object of the invention is to provide a method of using a solubilized and stabilized liquid formulation for increasing weight gain, improving the efficiency of feed utilization, increasing leanness, decreasing lipogenesis, increasing lipolysis, increasing muscle protein synthesis, decreasing muscle protein breakdown, or an improvement in carcass quality of the animal (including, but not limited to less fatty tissue, improved leanness, increased dressing percent and increased primal and lean cut yields) of a ruminant, a swine or a turkey comprising orally administering to the ruminant, swine or turkey an effective amount of a solubilized, stabilized liquid formulation comprising from 5 to 30% w/w of ractopamine or a physiologically acceptable salt thereof; from 20 to 90% w/w of a liquid nonionic cosolvent selected from polyethoxylated sorbitan fatty acid esters, polyethoxylated vegetable oils, or both; and, from 5 to 75% w/w water.

"Related substances" as used herein means reaction products, degradation products, or both, between ractopamine and cosolvents, diluents, excipients or nutritional ingredients, in the formulation of the present invention or when the formulation of the present invention is used to prepare a Type A medicated article, Type B or Type C medicated feed. It also includes any remaining starting material or intermediates from ractopamine synthesis and ractopamine dimers afforded by reaction between the reactive hydroxyl groups on two ractopamine molecules.

"Stabilized" as used herein, means chemical stability during storage as evaluated at, but not limited to, 25° C. for at least 3 months, preferably 6 months, more preferably 12 months, and most preferably 24 months where: 1) any new individual related substance does not exceed 0.2% w/w of the concentration of ractopamine in an aqueous combination of ractopamine or a physiologically acceptable salt thereof and a liquid nonionic cosolvent, as defined herein, 2) no individual related substance exceeds 1.5% w/w of the concentration of ractopamine in an aqueous combination of ractopamine or a physiologically acceptable salt thereof and a liquid nonionic cosolvent, as defined herein, and 3) the total related substances that may be afforded do not exceed 4% w/w of the concentration of ractopamine in an aqueous combination of ractopamine or a physiologically acceptable salt thereof and a liquid nonionic cosolvent, as defined herein.

The liquid nonionic cosolvents polyethoxylated sorbitan fatty acid esters or polyethoxylated vegetable oils useful in the present invention have a number average polyethoxylation of 4-40, preferably 15 to 25, more preferably 18-22. Examples of polyethoxylated vegetable oil includes polyethoxylated castor oil.

Solubilized stabilized liquid formulations of the present invention may comprise or may be used in the preparation of a liquid concentrate formulation referred to as a Type A medicated article as defined in the United States Code of Federal Regulations, Title 21, Section 558, incorporated herein by reference. As is known by those skilled in the art, a Type A medicated article may be used in the preparation of another Type A medicated article or a Type B or Type C medicated feed, both Type B and Type C are as defined in the United States Code of Federal Regulations, Title 21, Section 558, incorporated herein by reference. In Type A medicated articles, the active agent(s) are at a concentration higher than suitable for direct administration and require dilution to said direct administration amounts. Similarly, a Type B medicated feed may be used in the preparation of another Type B medicated feed or a Type C medicated feed. A Type B medicated feed is prepared by diluting a Type A medicated article or another Type B medicated feed. A Type C medicated feed is suitable for direct administration without the need for further mixing or dilution.

Since ractopamine is inherently basic, it readily forms acid addition salts with any number of inorganic and organic acids. These salts can be employed in the formulations, method and process of the present invention, and often are preferred to the free base, and are more conveniently formulated. Acids commonly employed to form acid addition salts include mineral acids such as hydrochloric acid, sulfuric acid, phosphoric acid, perchloric acid and the like; and organic acids such as acetic acid, citric acid, succinic acid, para-toluene sulfonic acid, methanesulfonic acid, lactic acid and the like. Preferred salts to be employed in the present method include the hydrochlorides and hydrobromides, and hydrochloride is most preferred.

The method of promoting growth, increasing weight gain, improving the efficiency of feed utilization, increasing leanness, decreasing lipogenesis, increasing lipolysis, increasing muscle protein synthesis, decreasing muscle protein breakdown, or an improvement in carcass quality of the animal (including, but not limited to less fatty tissue, improved leanness, increased dressing percent and increased primal and lean cut yields) is practiced by orally administering an effective amount of a solubilized stabilized liquid formulation as defined above to a ruminant, swine or turkey that receives a nutritionally adequate diet. The method generally will be practiced on ruminant, swine or turkey raised for human meat consumption, for example grower/finisher swine, turkey, cattle and the like. In a preferred embodiment, the method is practiced in swine or turkeys by administering a ractopamine formulation according to the present invention. Another preferred embodiment is practiced in ruminants such as cattle, sheep and goats, particularly cattle.

The method of the invention is preferably practiced by orally administering an effective amount of a solubilized stabilized liquid ractopamine formulation to an animal. The amount to be administered to an animal is an amount that is effective in promoting growth, improving leanness, increasing weight gain, improving the efficiency of feed utilization, increasing leanness, decreasing lipogenesis, increasing lipolysis, increasing muscle protein synthesis, decreasing muscle protein breakdown, or an improvement in carcass quality of the animal (including, but not limited to less fatty tissue, improved leanness, increased dressing percentage and increased primal and lean cut yields). The effective amount to be administered will vary somewhat depending upon the particular animal species being treated, but generally will be from about 1 to about 200 parts per million (ppm) of total daily feed intake. A preferred embodiment employs about 2 to about 100 ppm of total daily feed and more preferably from about 3 to about 50 ppm of total daily feed. A typical amount of active ingredient to be administered to ruminants will be from about 2 to about 40 ppm of total daily feed intake, and preferably from about 3 to about 30 ppm of total daily feed intake. A typical amount of active ingredient to be administered to swine will be from about 2 to about 40 ppm of total daily feed intake, and preferably from about 3 to about 30 ppm of total daily feed intake. Also, a typical amount of active ingredient to be administered to turkeys will be from about 2 to about 40 ppm of total daily feed intake, and preferably from about 3 to about 30 ppm of total daily feed intake.

While the formulations described herein are effective in promoting average daily weight gain and improving feed efficiency in animals, they also cause observable improvement in the quality of the meat produced. For example, formulations containing ractopamine appear to mobilize free fatty acids from fatty tissue and depress the deposition of fat as the animals gain weight. This reduction of fat is beneficial since the animal being treated according to the invention gains weight in the form of more useable lean meat, thereby reducing waste and improving the value of the animal thus treated.

Generally, liquid Type A medicated articles can be mixed into either liquid or dry supplements or into final feeds. A concentrated liquid Type A medicated article or liquid. Type B medicated feed, may be applied to dry feeds through a dribble bar in the mixer, by spraying onto the feed while mixing, or by microingredient machines. It is believed the present solubilized stabilized liquid concentrate may be mixed into liquid feed supplements or sprayed onto dry feeds or dispensed by conventional microingredient machines, such as U.S. Pat. No. 4,733,971, designed to accommodate liquid formulations.

Type B medicated feed may be liquid or dry and is intermediate between a Type A medicated article and a Type C medicated feed, which is a complete feed to be fed directly to animals. The Type B formulation contains a substantial quantity of nutrients, including vitamins and/or minerals and/or other nutritional ingredients in an amount not less than 25% by weight of the formulation. The amount of Category I pharmacologically active agent in Type B medicated feeds cannot exceed 200 times the maximum daily use level in a final feed or Type C medicated feed. Category I is the designation used by the United States Code of Federal Regulations for those active agents, e.g., ractopamine, for which no withdrawal period is required at the lowest use level in each species for which they are approved.

The composition of Type B medicated feeds varies from physiologically acceptable diluents to conventional concentrates designed to provide protein, vitamins, minerals, amino acids, or other nutritive ingredients. Type B medicated feeds may be a simple mix of a drug with suitable diluents, in which case the main concerns are homogeneity, segregation during transport and chemical stability.

Liquid feed supplements (LFS) are a Type B article and have become an increasingly important means of supplementing the nutrition of cattle in the United States. In certain areas, 50% or more of the feed lot cattle are fed LFS. As a result, LFS have become a convenient method of delivering drugs to cattle provided the drug is physically and chemically stable in the LFS. The composition of LFS varies widely depending on locally available byproducts and relative cost of other ingredients. Consequently, great differences exist in nutritional content, specific gravity, dissolved solids content, pH, viscosity and thixotropy.

Two basic types of LFS are marketed to the cattle industry, a conventional liquid formulation and a thixotropic formulation. The thixotropic formulation becomes quite fluid when agitated but becomes viscous or forms a soft gel within a few minutes to an hour after agitation is discontinued. LFS containing a drug(s) are generally agitated immediately prior to use even if it has been demonstrated that the drug is positionally (physically) stable throughout the batch and does not settle to the bottom or float to the surface during the storage period. If the drug is soluble in the continuous phase of the LFS, then it would be expected to be positionally stable, but agitation immediately prior to use is typically still recommended.

For suspensions, the smaller the diameter of the drug particles and the more viscous the formulation, the slower the rate of settling. Xanthan gum, certain carbohydrates, pectin, and other viscosity-building agents may be used to increase the viscosity of conventional LFS formulations such that the settling is not significant during the expected shelf life of the product. Agents such as attapulgite clay can be used to manufacture thixotropic formulations which have good flow properties when being pumped or sheared, but will have sufficient viscosity when not being agitated to maintain in suspension minerals, drugs, and other solid matter which would otherwise settle.

Each of the Type A, Type B and Type C medicated articles and feeds of the present invention are prepared using art recognized conventional mixers and microingredient systems, associated manufacturing equipment and techniques from the liquid formulations of the present invention. Mixers are commercially available in many sizes, shapes, designs and configurations, such as horizontal mixers, including dual shafted paddle mixers. Microingredient systems, such as U.S. Pat. No. 4,733,971, are also commercially available.

Both manual and automatic methods are used to medicate the drinking water of animals. Manual methods for adding drug to drinking water vary from placing a single dose of drug in a trough of water for an animal to medicating a header tank designed to provide water for a large number of animals. Typically, the instructions on containers of drinking water medication indicate to dissolve or dilute the entire contents in a specified quantity of water.

Products designed to medicate drinking water generally contain instructions to prepare a stock solution which is further diluted in the final drinking water either manually or using devices called proportioners, such as a Dosatron™. A proportioner is a device which pumps a precise quantity of stock solution into a chamber where it is mixed with the water flow before passing through the outlet to the animal drinking station. Because of its volumetric design, the injector or proportioner device maintains a constant ratio of concentrate to water flow irrespective of water pressure and water flow. Most proportioners are designed so that the ratio of drug concentrate to water can be varied depending on the drug to be used and the intended drug concentration in the final drinking water. For example, the ratio of a drug stock solution to water can be varied from 1:10 to 1:500.

Coloring agents may be used in solution concentrates. Two reasons for including a coloring agent in the formulation are to identify the final drinking water as being medicated and to uniquely identify the product.

Lick tanks, such as U.S. Pat. No. 5,335,625, have found utility in delivering nonprotein nitrogen, vitamins, minerals, and other nutrients, as well as drugs to pasture and diary cattle. For a formulation to be used in a lick tank, all of the ingredients must remain dissolved over a range of temperatures, or, if the formulation is thixotropic, the ingredients should not settle or separate while in the lick tank. Typical ingredients in a lick tank formulation include corn steep liquor, molasses, condensed whey, condensed molasses solubles, brewers' condensed solubles, condensed distillers solubles, urea, salt, phosphoric acid, sulfur acid, dispersible vitamins, and soluble minerals.

The invention further relates to a process for preparing soluble, stable concentrated liquid feeds, liquid vitamin concentrates and drinking water compositions containing ractopamine or a physiologically acceptable salt thereof, a liquid nonionic cosolvent selected from polyethoxylated sorbitan fatty acid esters, polyethoxylated vegetable oils, or both, and water comprising admixing a solubilized stabilized liquid formulation of the present invention with a liquid feed, a water soluble liquid concentrate, a dry water soluble carrier, or with drinking water to afford a substantially homogenous and chemically stable composition.

The present invention further contemplates a process for preparing a dry, solid feed comprising combining a solubilized stabilized liquid formulation of the present invention containing ractopamine or a physiologically acceptable salt thereof, a liquid nonionic cosolvent selected from polyethoxylated sorbitan fatty acid esters, polyethoxylated vegetable oils, or both, and water to a dry animal feed which may be administered to animals or diluted with dry animal feed matter to afford a ractopamine or a physiologically acceptable salt thereof complete feed composition.

Example 1 (Comparative)

An example of a formulation in which solubility can be achieved in excess of 25% w/w ractopamine is a vehicle system using either 100% propylene glycol (PG) or an aqueous vehicle system containing PG. A formulation in which the vehicle system is 50% PG and 50% water would be capable of dissolving at least 10% ractopamine at 25° C. PG is an excellent solvent for ractopamine and is "generally recognized as safe" (GRAS) in Title 21 Code of Federal Regulations 582.1666. In addition the viscosity of aqueous PG formulations is generally within an acceptable range to be easily applied to animal feeds. Depending upon the ratio of water to PG in the formulation, the solution will not freeze in climates commonly found in livestock producing areas of the United States. Thus, PG would be an excellent choice of a solvent or vehicle for solubilization of ractopamine for administration to livestock. However, new related substances form slowly during storage of propylene glycol solutions of ractopamine at normal room temperature (~25° C.). The PG reacts with the ethan-1,2 diyl hydroxy group of the various isomers of ractopamine (compound of formula I) to form covalently bonded related substances of formula II. The reaction shown below is not reversible under normal storage conditions:

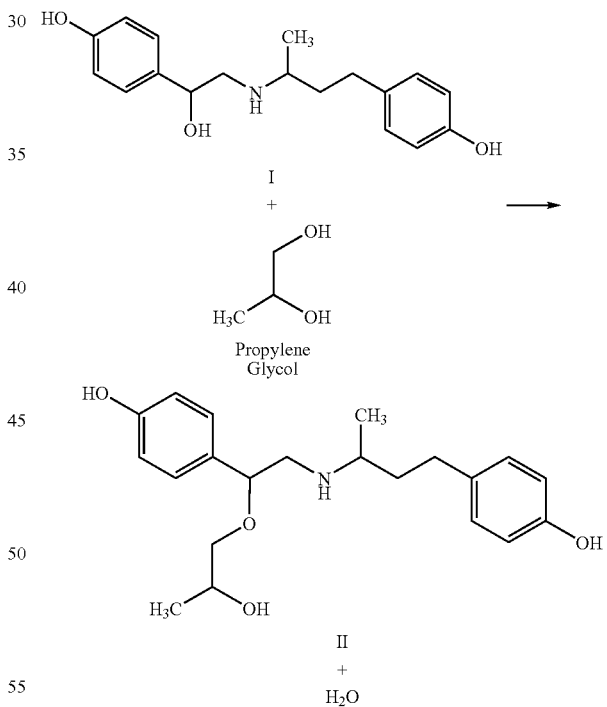

Thus, even though PG is an excellent solvent and vehicle system for preparing high concentrations (4% to greater than 25%) of ractopamine, PG is unacceptable as a solvent in liquid ractopamine formulations because of the irreversible formation of reaction product related substances.

Example 2 (Comparative)

Solution formulations containing high concentrations (>20%) of ractopamine can be achieved in a vehicle system containing polyethylene glycol (PEG) 200, PEG 300, or both. Toxicology properties, viscosity and the bland nature of the PEGs make the PEGs acceptable solvents and vehicle systems for use in liquid livestock formulations. However, as described in Example 1, the hydroxyl groups on the PEG molecular structure react with the ethan-1,2 diyl hydroxy group of the various isomers of ractopamine to form covalently bonded related substances. The reaction is not reversible under normal storage conditions. Thus, even though the PEGs are excellent solvents and vehicle systems for preparing liquid formulations containing 4% to greater than 20% of ractopamine, the PEGs are unacceptable as solvents in liquid ractopamnine formulations.

Example 3 (Comparative)

Example 3 consists of lists of liquid agents from various chemical classes that have been investigated as potential solvents or cosolvents for ractopamine. Not all of the liquid agents in the lists below would be suitable for use in livestock feed but serve as examples of liquid agents which demonstrate one or more of 1) insufficient solvent power to achieve a 10% solution of ractopamine; 2) result in unacceptable degradation of ractopamine to afford related substances; or 3) result in the formation of unacceptable reaction product related substances.

Solubility determinations are performed in 1-dram vials. Add ractopamine HCl to a vial containing a liquid agent to give a final w/w ratio of 10% ractopamine HCl to liquid agent. Mix the solution vigorously on a vortex mixer for 2 to 6 minutes. After the mixing period, visually, assess whether the ractopamine dissolves in the liquid agent or whether insoluble material (cloudy solution or two distinct phases) remains in the vial. If the solubility is less than 10%, add additional liquid agent to dilute the ractopamine HCl to a 5-8% range. Repeat the mixing procedure and assess whether the ractopamine is soluble in the liquid agent or whether it remains insoluble at the lower concentration. Apply heat (from room temperature up to 60° C.) as needed to aid solubilization. Allow heated samples to cool to room temperature to assess solubility by visual observation for precipitant or cloudiness.

Tables 1 and 2 below summarize the results of the solubility, stability, or both, for ractopamine HCL in the solvents tested. Table 1 summarizes the solvents where ractopamine HCl is soluble but has unacceptable stability. Table 2 summarizes the solvents where ractopamine HCl is insufficiently soluble. Solubility is low in many "non-hydroxyl" solvents and oils.

TABLE 1

Solvents where ractopamine HCl is soluble but has unacceptable stability

| Solvent | Solubility @ RT | Comment |
|---|---|---|
| Propionic Acid (20% solution) Fisher Scientific | ≧10% | Stability discontinued - generated a number of large related sub peaks. |
| Acetic Acid Glacial (50% solution) Mallinckrodt, Inc | ≧10% | Must buffer pH in 10% ractopamine formulation. Stability discontinued generation of new related subs in stability storage. |

TABLE 1-continued

Solvents where ractopamine HCl is soluble but has unacceptable stability

| Solvent | | Solubility @ RT | Comment |
|---|---|---|---|
| Lactic Acid (85% solution) Fisher Scientific | | ≦10% | 10% ractopamine formulation possible by heating and buffering pH. Stability discontinued generation of new related subs in stability storage. |
| Maleic Acid (20% Solution) Fisher Scientific | | ≦10% | |
| Tetrahydrfurfuryl Alcohol (THFA) | | ≦10% | |
| Ethylenediamine | | ≧20% | pH very alkaline |
| Ethanolamine | | ≧10% | pH very alkaline |
| Methanol, Fisher Scientific | | ≧10% | Methanol reacts with ractopamine to form methoxy ractopamine related substance |
| Ethylene Glycol | | ≧10% | Potential for generation of new related subs. |
| Diethylene Glycol | | ≧10% | Potential for generation of new related subs |
| Monomethylated Polyethylene Glycol MPEG 350, Union Carbide Corporation | Neat 50/50 water | ≦10% ≧10% | 10% ractopamine formulations possible with ratio of (MPEG 350 or 500) to water at 50/50 or heating. |
| Monomethylated Polyethylene Glycol MPEG 550, Union Carbide Corporation | Neat 50/50 water | ≦10% ≧10% | MPEG solvents generated a number of new related sub peaks in stability studies |
| Diethylenetriamine (DETA) | | ≧10% | Very alkaline pH |
| Polyethylene Glycol PEG 200 Acros Organics | Neat 50/50 water | ≦10% ≧10% | 10% ractopamine formulations possible with ratio of (PEG 200 or 300) to water at 50/50 or heating. |
| Polyethylene Glycol PEG 300 Acros Organics | Neat 50/50 water | ≦10% ≧10% | PEG solvents generated a number of new related sub peaks in stability studies |
| Polyethylene Glycol PEG 400 Acros Organics | Neat (Viscous) | ≦10% | |
| Block Copolymer (Pluronic ® L61, BASF Corporation | Neat (Viscous) 50/50 water | ≦10% ≧10% | 10% ractopamine formulation possible with ratio of Pluronic ® L61 to water at 50/50 generated a number of new related substance peaks in stability studies. |

TABLE 2

Solvents where ractopamine HCl is insufficiently soluble

| Solvent | Solubility @ RT |
|---|---|
| 1-Methyl-2-Pyrrolidinone Pharmasolve ®, ISP Technologies, Inc. | <5% |
| Caprylic/capric triglyceride Migylol ® 810, hüls Petrarch Systems | <8% |
| Medium chain triglyceride Migylol ® 812, hüls Petrarch Systems | <8% |
| Triglyceride of caprylic/capric and succinic acid Migylol ® 829, hüls Petrarch Systems | <8% |

TABLE 2-continued

Solvents where ractopamine HCl is insufficiently soluble

| Solvent | Solubility @ RT |
|---|---|
| Propylene glycol diester of caprylic/capric acid Migylol ® 840, hüls Petrarch Systems | <8% |
| 2-Pyrrolidone | ≦5% |
| 2-Pyrol ®, ISP Technologies, Inc. | |
| Glycerol Formal | ≦5% |
| Sigma Chemical Company | |
| Triacetin | <5% |
| Sigma Chemical Company | |
| Isopropyl Myristrate, | <8% |
| Emerest ® 2314, Henkel Corporation | |
| Methyl Oleate | <8% |
| Emery ® 2301, Henkel Corporation | |
| Methyl Caprylate-Caprate | <8% |
| Emery ® 2209, Henkel Corporation | |
| Dimethyl Isosorbide | <8% |
| Sigma Chemical Company | |
| Soybean Oil Methyl Ester | <8% |
| Soy Gold ® 2000, AG Environmental Products, LLC | |
| Corn Oil | <8% |
| Mazzola ® Corn Oil, Best Foods Division, CPC International, Inc. | |
| Sunflower Oil | <8% |
| Wesson ® Sunflower Oil, Hunt-Wesson, Inc. | |
| Ethyl Lactate, Eastman Kodak Company | <5% |
| Hexane, EM Science | <5% |
| Oleic Acid | <5% |
| Priolene ™ 6933, Uniqema | |
| Nonylphenol Ethoxylate, POE-10 | <5% |
| Makon ® 10, Stepan Company | |
| Mono-diglyceride of caprylic/capric fatty acids Capmul ® MCM, Abitec Corporation | <8% |
| N,N, Dimethylacetamide | <5% |
| Fisher Scientific | |
| Petroleum Ether | <5% |
| EM Science | |
| β-Cyclodextrin Sulfbutyl Ether 7 Sodium Salt 20% Solution Captisol ™, CyDex, Inc. | <10% |
| Hydroxypropyl β-Cyclodextrin (Trappsol ® Cyclodextrin, Technologies, Development, Inc. | <10% |
| Propylene Carbonate | <5% |
| Fisher Scientific | |
| Ethyl Acetate | <5% |
| Fisher Scientific | |
| Oleoyl Macrogolglycerides EP | <5% |
| Labrafil ® M 1944 CS, Gattefossé Corporation | |
| Caprylic/Capric Triglycerides, BP, FP Labrafac ® CC, Gattefossé Corporation | <5% |
| Glyceryl and polyethylene glycol esters Labrasol ®, Gattefossé Corporation | <5% |
| Propylene Glycol Laurate | <5% |
| Lauroglycol ® FCC ®, Gattefossé Corporation | |
| Citric Acid (50% solution) | <5% |
| Sigma Chemical Company | |
| Benzoic Acid (0.3% solution) | <10% |
| Fisher Scientific | |
| Glutamic Acid (20% solution) | <5% |
| Aldrich Chemical Company, Inc. | |
| D-Gluconic Acid | <10% |
| Sigma Chemical Company | |
| D-Glucuronic Acid (20% solution) | <5% |
| Sigma Chemical Company | |
| L-Malic Acid (20% solution) | <5% |
| Aldrich Chemical Company, Inc. | |
| Fumaric Acid | <5% |
| Sigma Chemical Company | |
| Malonic Acid | ≧5% |
| Sigma Chemical Company | |
| Phosphoric Acid (85% Solution) | <5% |
| Mallinckrodt, Inc | |
| Succinic Acid (5% Solution) | <5% |
| Sigma Chemical Company | |
| L-Tartaric Acid 20% solution | <5% |
| Aldrich Chemical Company, Inc. | |
| Mineral Oil, QA246U Eli Lilly and Company | <5% |
| 2-pyrrolidinone, 1-Octyl 2-Pyrrolidinone, 1- | <5% |
| Ethenylhexadecyl-, Homopolymer Sulfuric Acid Monododecyl Ester Sodium Salt Agrimax ™ 3, ISP Technologies, Inc. | |
| Forward ® DC | <5% |
| S. C. Johnson Commercial Markets, Inc. | |
| Benzyl Alcohol | ≧5% |
| Aldrich Chemical Company, Inc. | |
| Polyglycol P-2000 | <5% |
| Dow Chemical Company | |
| Aromatic 200 | <5% |
| SC Solvent 200, ChemCentral Corporation | |
| Glycol Ether PM, ChemCentral Corporation) | <5% |
| Aromatic 100 | <5% |
| Vanwaters and Rogers, Inc. | |
| Gamma Butylactone | <5% |
| BASF Corporation | |
| Amyl Acetate | <5% |
| AgsolEx ™ 8, ISP Technologies, Inc. | <5% |
| Petroleum distillates (naphtha) | <5% |
| Panasol AN-2K, Standard Oil | |
| Centrapour ® Clear Fry Oil | <5% |
| Central Soya Company, Inc. | |
| 1,3 Dioxolane, | <5% |
| Ferro Corporation | |
| 4-Methyl-1-3Dioxolane | <5% |
| Ferro Corporation | |
| Polyethylene Glycol Dimethyl Ether DMPEG-350, Ferro Corporation | <5% |
| Tetrahydrofuran (THF) | <10% |
| Acetone | <10% |
| Dichloromethane | <10% |
| Ethyl Alcohol | <10% |
| 1-Butanol | <10% |
| Trichloroethylene | <10% |
| Dipropylene glycol n-butyl ether | <10% |
| Cyclohexanone | <10% |
| Acetophenone | <10% |
| Isophorone | <10% |
| Toulene | <10% |
| Acetaldehyde Phenethyl Propyl Acetal (Acetal R), Aldrich Chemical Company | <10% |
| Block Copolymer Pluronic ® L31, BASF Corporation | ≦10% |

The Pluronic L-61 samples, beginning with the 3 month timepoint and ending with the 24 month timepoint at 30° C. and 40° C., were evaluated for new related substances. Under these conditions, new related substances were above 0.2% at 24 months. There were nine new related substances detected at 24 months. The two new related substances of interest were number 2 and number 8 (in chronological retention sequence) which will be referred to as rel. sub. (2) and rel. sub. (8). Rel. sub. (2) was less than 0.09% through 12 months and increased to 0.13% and 0.22% at 18 and 24 months, respectively. Rel. sub. (8) was at 0.11% at 0.5 months at 40° C. For the remaining timepoints at 30° C., rel. sub. (8) was at 0.14% at 3 months, 0.24% at 6 months, 0.3% at 9 months, 0.5% at 12 months, 0.6% at 18 months, and 0.41% at 24 months. Refrigerated storage at 5° C. largely suppressed the formation of rel. sub. (2) and rel. sub. (8) for the 24 month duration of the stability study.

Example 4

Table 3 summarizes the solvents where ractopamine is both soluble and stable under the procedures described in Example 3.

TABLE 3

Solvents where ractopamine HCl is soluble and stable

| Solvent | | Solubility @ RT | Comment |
|---|---|---|---|
| Polyoxyethylene-20-Sorbitan Monolaurate (Tween 20, Fisher Scientific) | Neat (Viscous) 50/50 water | ≦10% ≧10% | 10% ractopamine formulations with ratios of Polyoxyethylene 20 Sorbitan Monolaurate to water below 50/50 precipitate after prolonged storage at 5° C. |
| Polyoxyethylene-20-Sorbitan Monooleate (Tween 80, Fisher Scientific | Neat (Viscous) 50/50 water | ≦10% ≧10% | 10% ractopamine formulations with ratios of Polyoxyethylene-20-Sorbitan Monooleate to water below 50/50 precipitate after prolonged storage at 5° C. |
| Polyoxyl 35 Castor Oil (Cremophor EL, BASF Corporation) | Neat (Viscous) 50/50 water | ≦10% ≧10% | 10% ractopamine formulations with a ratio of Polyoxyl 35 Castor Oil to water at 50/50 are somewhat viscous and precipitate after short term (3 months) storage at 5° C. |

Example 5

It is known by those skilled in the art, that surfactants such as polyethoxylated sorbitan fatty acid esters may increase the solubility of some compounds. However, the long term stability of solution formulations of ractopamine HCl dissolved in aqueous vehicle systems containing polyoxyethylene 20 sorbitan monolaurate (PSL) was an unexpected discovery. Polyoxyethylene 20 sorbitan monolaurate is commonly used in foods, is GRAS, is a laurate ester of sorbitol and its anhydrides copolymerize with approximately 20 moles of ethylene oxide for each mole of sorbitol and sorbitol anhydrides. The resulting ester contains many hydroxyl moieties which would be expected to react with the ethan-1,2 diyl hydroxy group of ractopamine in a similar fashion as Examples 1 and 2 above. However, surprisingly, the hydroxyl moieties of PSL do not react with ractopamine to form new related substances (<0.2%) during storage for up to 24 months at 25° C. and 12 months at 40° C. By varying the ratio of PSL to water from 90:10 to 10:90 w/w various concentrations of ractopamine solutions can be prepared. The most preferred ratio is 50:50 w/w which results in a solubility of greater than 10% ractopamine and a viscosity which facilitates application to animal feeds. A ratio of >40% PSL is needed to achieve a 10% solubility of ractopamine particularly at colder temperatures, for example, 5° C.

A formulation containing PSL and ractopamine HCL is manufactured by adding 50.44 g of a ractopamine aqueous slurry (21.5% ractopamine HCl), 48.80 g of PSL and 9.25 g of water. Weigh the ractopamine slurry in a suitable beaker and add PSL and water. Apply sufficient heat (≦60° C.) to the beaker with stirring to afford rapid solubilization of ractopamine. The resulting formulation is stable for at least 24 months at 5° C. and 25° C. and for at least 12 months at 40° C.

Formulations containing 10% by weight ractopamine and PSL:water w:w at 40:60 and 50:50 were evaluated for new related substances by comparing the chromatogram obtained at time zero to that obtained after storage for 24 months at 30° C. at pH 4.0, 5.0, 6.0 and 7.0. The pH was adjusted using 2N sodium hydroxide. A relative retention time was calculated using 4-(p-hydroxy phenyl)-butan-2-one as a marker. This compound is a starting material for ractopamine synthesis and is typically the largest individual related substance in ractopamine aqueous slurry (from the synthesis) and is easily identified in chromatograms.

At pH 4.0, the total related substances and largest individual related substance at time zero were 1.22 and 0.41 percent, respectively and 4-(p-hydroxy phenal)-butan-2-one was the largest individual related substance. At 24 months, total related substances increased to 2.55 percent. The increase was driven mostly by the increase in ractopamine dimers from 0.06 percent at time zero to 0.89 percent at 24 months. The dimers were the largest individual related substance at 24 months. Two related substances not readily detectable at time zero were detectable at 24 months. The first related substance peak relative retention time (peak releative retention time) (rrt=0.69) assayed at 0.08 percent and the second related substance (rrt=0.76) assayed at less than 0.02 percent.

At pH 5.0, the total related substances and largest individual related substance at time zero were 1.22 and 0.41 percent, respectively and 4-(hydroxy phenyl)-butan-2-one was the largest individual related substance. At 24 months, total related substances increased to 2.96 percent. The increase was driven mostly by the increase in ractopamine dimers from less than 0.01 percent at time zero to 1.28 percent at 24 months. The dimers were the largest individual related substance at 24 months. Two related substances not readily detectable at time zero were detectable at 24 months. The first related substance (rrt=0.42) assayed at less than 0.02 percent and the second related substance (rrt=0.76) also assayed at less than 0.02 percent.

At pH 6.0, the total related substances and largest individual related substance at time zero were 1.20 and 0.40 percent, respectively. The compound 4-(p-hydroxyphenyl)-butan-2-one was the largest individual related substance. At 24 months, total related substances increased to 4.13 percent. The increase was driven mostly by the increase in ractopamine dimers from 0.10 percent at time zero to 1.82 percent at 24 months. The dimers were the largest individual related substance at 24 months. Five related substances not readily detectable at time zero were detectable at 24 months. The first related substance (rrt=0.69) assayed at 0.12 percent, the second related substance (rrt=0.76) assayed at less than 0.02 percent, the third related substance (rrt=1.24) assayed at 0.08 percent, the fourth related substance (rrt=1.34) assayed at less than 0.01 percent, and the final related substance (rrt=1.35) assayed at less than 0.18 percent.

Example 6

Polyoxyethylene 20 sorbitan monooleate (PSO) is commonly used in foods, is GRAS, is an oleate ester of sorbitol and its anhydrides copolymerize with approximately 20 moles of ethylene oxide for each mole of sorbitol and sorbitol anhydrides. The resulting ester contains many hydroxyl moieties similar to PSL in Example 4 above. However, as in Example 5 above, PSO does not react with ractopamine to form new (<0.2%) related substances during storage for up to 24 months at 25° C. By varying the ratio of PSO to water from 90:10 to 10:90 w/w various concentrations of ractopamine solutions can be prepared. The preferred ratio is 50:50 w/w which results in a solubility of greater than 10% ractopamine HCl and a viscosity which facilitates application to animal feeds. 10% ractopamine formulations with ratios of PSO to water below 50/50 w/w will precipitate out under 5° C. storage, and ratios exceeding 60/40 (PSO/water) w/w would be less preferred due to high viscosity.

A formulation containing PSO and ractopamine HCl is manufactured by adding 69.78 g ractopamine aqueous slurry (21.5% ractopamine), 67.5 g PSO and 12.72 g water. Weigh the ractopamine slurry into a suitable beaker and add PSO and water. Apply sufficient heat ($\leq 60°$ C.) to the beaker with stirring to afford rapid solubilization of the ractopamine. The resulting formulation is stable for at least 24 months at 25° C. In addition samples stored at 5° C. remains in solution for at least 12 months indicating excellent solubility at temperatures as low as 5° C.

Example 7

Polyoxyl 35 Castor Oil (PCO) is a non-ionic solubilizer and emulsifier obtained by causing ethylene oxide to react with castor oil. The main component is glycerol-polyethylene glycol ricinoleate with smaller amounts of polyethylene glycol ricinoleate and the corresponding free glycols. Polyoxyl 35 Castor Oil is listed in the United States Pharmacopeia/National Formulary. By varying the ratio of PCO to water from 90:10 to 10:90 w/w various concentrations of ractopamine solutions can be prepared. The most preferred ratio is 50:50 w/w which results in a solubility of greater than 10% ractopamine HCl. The formulation is somewhat viscous but can be applied to animal feeds with suitable equipment such as appropriately sized spray nozzles or dibble bars and sufficient pumping pressure to deliver the formulation to the mixer employed to mix the ractopamine solution into the feed. Dilution of the formulation by the water in a microingredient machine would also be an effective technique for applying the formulation to animal feed followed by thorough mixing in a suitable mixer such as a horizontal ribbon blender. Ten percent ractopamine formulations with ratios of PCO to water below 50/50 w/w will precipitate out under 5° C. storage, and ratios exceeding 60/40 (PSO/water) w/w would be less preferred due to high viscosity.

A formulation containing PCO and ractopamine HCl is manufactured by adding 69.78 g ractopamine aqueous slurry (21.5% ractopamine), 67.5 g PCO and 12.72 g water. Weigh the ractopamine slurry into a suitable beaker and add PCO and water. Apply sufficient heat ($\leq 60°$ C.) to the beaker with stirring to afford rapid solubilization of the ractopamine. The resulting formulation is chemically stable for at least 24 months at 25° C. and did not precipitate out of solution; Samples stored at 5° C. remain clear during 3 months storage. At the 6 month timepoint a precipitate was observed in the sample. A formulation with 50:50 ratio of PCO to water is both physically and chemically stable for 24 months at 25° C.

The formulation containing PCO, ractopamine and water (10% ractopamine and 50/50 cosolvent/water) was evaluated for new related substances by comparing the chromatogram obtained at time zero to that obtained after 24 months at 30° C. The total related substances and most abundant individual related substance at time zero were 1.2 and 0.4%, respectively. The most abundant individual related substance was 4-(p-hydroxy phenyl)-butan-2-one. At 24 months, total related substances increased to 2.5%. The most abundant individual related substance was 4-(p-hydroxy phenyl)-butan-2-one at 0.4%. Ractopamine dimers increased from 0.07% at time zero to 0.6% at 24 months. Four related substances not readily detected at time zero were detected at 24 months. These new related substances ranged from 0.03 to 0.13% and summed to 0.29%. One of these exceeded 0.1% and none exceeded 0.2%.

We claim:

1. A solubilized stabilized liquid formulation comprising from 10 to 30% w/w of ractopamine or a physiologically acceptable salt thereof; from 20 to 90% w/w of a liquid nonionic cosolvent selected from polyethoxylated sorbitan fatty acid esters, polyethoxylated vegetables oils, or both; and 5 to 75% w/w water.

2. The solubilized stabilized liquid formulation of claim 1 comprising 10 to 20% w/w ractopamine or a physiologically acceptable salt thereof, 30 to 80% w/w of a liquid nonionic cosolvent selected from polyethoxylated sorbitan fatty acid esters, polyethoxylated vegetable oils or both, and 10 to 60% w/w water.

3. The solubilized stabilized liquid formulation of claim 1 comprising 10 to 15% ractopamine or a physiologically acceptable salt thereof; from 40 to 55% liquid nonionic cosolvent selected from polyethoxylated sorbitan fatty acid esters, polyethoxylated vegetable oils, or both; and 35 to 50% water.

4. The solubilized stabilized liquid formulation of claim 3 wherein the nonionic cosolvent is a polyethoxylated sorbitan fatty acid ester.

5. The solubilized stabilized liquid formulation of claim 3 wherein the nonionic cosolvent is a polyethoxylated vegetable oil.

6. The solubilized stabilized liquid formulation of claim 4 wherein the nonionic cosolvent is polyoxythylene 20 sorbitan monolaurate.

7. The solubilized stabilized liquid formulation of claim 6 wherein ractopamine or a physiologically acceptable salt thereof is ractopamine hydrochloride.

8. A process for preparing a solubilized stabilized liquid formulation comprising:
    admixing ractopamine or a physiologically acceptable salt thereof with water and a liquid nonionic cosolvent selected from polyethoxylated sorbitan fatty acid esters, polyethoxylated vegetable oils, or both; and heating the mixture to no higher than 100° C. to afford a stabilized and solubilized formulation comprising from 10 to 30% w/w ractopamine or a physiologically acceptable salt thereof; from 20 to 90% w/w of a liquid nonionic cosolvent selected from polyethoxylated sorbitan fatty acid esters, polyethoxylated vegetable oils, or both; and, from 5 to 75% w/w water.

9. A method of increasing weight gain, improving the efficiency of feed utilization, increasing leanness, decreasing lipogenesis, increasing lipolysis, increasing muscle protein synthesis, decreasing muscle protein breakdown, or an improvement in carcass quality of a ruminant, a swine or a turkey comprising administering to the ruminant, swine or turkey an effective amount of a solubilized stabilized liquid formulation of claim 1.

* * * * *

UNITED STATES PATENT AND TRADEMARK OFFICE
CERTIFICATE OF CORRECTION

PATENT NO. : 7,943,670 B2
APPLICATION NO. : 10/571437
DATED : May 17, 2011
INVENTOR(S) : Michael David Burton, Sr. et al.

Page 1 of 1

It is certified that error appears in the above-identified patent and that said Letters Patent is hereby corrected as shown below:

On title page, after item (65) and immediately before item (51), please insert item (60) as follows:

--Related U.S. Application Data
Provisional application No. 60/509,348, filed on Oct. 7, 2003.--

On title page, column 2, item (56), under the heading "OTHER PUBLICATIONS", please replace the text "Watkins et al," with the text --Watkins et al.--

In column 1, line 3, after the title "LIQUID FORMULATIONS OF RACTOPAMINE" and immediately before the heading "BACKGROUND OF THE INVENTION", please insert --This is the national phase application, under 35 USC 371, for PCT/US2004/030902, filed 4 October 2004, which claims the benefit, under 35 USC 119(e), of US provisional application 60/509,348, filed 7 October 2003.--

In claim 2, column 16, line 18, please replace the text "oils" with the text --oils,--

In claim 6, column 16, line 32, please replace the text "polyoxythylene" with the text --polyoxyethylene--

Signed and Sealed this
Second Day of August, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,943,670 B2 | Page 1 of 1 |
| APPLICATION NO. | : 11/571437 | |
| DATED | : May 17, 2011 | |
| INVENTOR(S) | : Michael David Burton, Sr. et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 908 days.

Signed and Sealed this

Eighth Day of November, 2011

David J. Kappos
*Director of the United States Patent and Trademark Office*